United States Patent
Carlucci et al.

(10) Patent No.: US 6,735,804 B2
(45) Date of Patent: May 18, 2004

(54) TOOTHBRUSH BRISTLE DISK

(75) Inventors: Vito James Carlucci, Stratford, CT (US); Paul Joseph Denhup, Stratford, CT (US)

(73) Assignee: Conair Corporation, Stamford, CT (US)

( * ) Notice: Subject to any disclaimer, the term of this patent is extended or adjusted under 35 U.S.C. 154(b) by 137 days.

(21) Appl. No.: 10/044,797

(22) Filed: Jan. 10, 2002

(65) Prior Publication Data

US 2002/0108194 A1 Aug. 15, 2002

Related U.S. Application Data

(60) Provisional application No. 60/261,452, filed on Jan. 12, 2001.

(51) Int. Cl.$^7$ ............................................. A61C 17/22
(52) U.S. Cl. ........................ 15/28; 15/167.1; 15/180; 15/DIG. 5
(58) Field of Search ..................... 15/22.1, 28, 167.1, 15/180, DIG. 5

(56) References Cited

U.S. PATENT DOCUMENTS

| | | | |
|---|---|---|---|
| 2,080,605 A | 5/1937 | Duey | 15/167.1 |
| 2,558,332 A | 6/1951 | Artale | 15/167.1 |
| 3,196,299 A | 7/1965 | Kott | 310/81 |
| 3,577,579 A | 5/1971 | Duve | 15/22.1 |
| 3,667,454 A | 6/1972 | Prince | 601/18 |
| 3,685,080 A | 8/1972 | Hubner | 15/22.1 |
| 4,399,582 A | 8/1983 | Ernest et al. | 15/176.4 |
| 4,709,438 A | 12/1987 | De Tavares | 15/167.1 |
| 4,995,131 A | 2/1991 | Takeda | 15/22.1 |
| 5,099,536 A | 3/1992 | Hirabayashi | 15/28 |
| 5,170,525 A | 12/1992 | Cafaro | 15/28 |
| 5,173,983 A | 12/1992 | Le | 15/28 |
| 5,289,604 A | 3/1994 | Kressner | 15/22.1 |
| 5,341,534 A | 8/1994 | Serbinski et al. | 15/22.1 |
| 5,365,627 A | 11/1994 | Jousson et al. | 15/22.1 |
| 5,383,242 A | 1/1995 | Bigler et al. | 15/22.1 |
| D361,433 S | 8/1995 | Yang | D4/101 |
| 5,461,744 A | 10/1995 | Merbach | 15/22.1 |
| 5,465,444 A | 11/1995 | Bigler et al. | 15/22.1 |
| 5,467,495 A | 11/1995 | Boland et al. | 15/28 |
| 5,504,961 A | 4/1996 | Yang | 15/28 |
| 5,577,285 A | 11/1996 | Drossler | 15/22.1 |
| 5,617,601 A | 4/1997 | McDougall | 15/22.1 |
| 5,625,916 A | 5/1997 | McDougall | 15/28 |
| 5,652,990 A | 8/1997 | Driesen et al. | 15/28 |
| 5,706,542 A | 1/1998 | Okada | 15/22.1 |
| 5,732,432 A | 3/1998 | Hui | 15/22.1 |
| 5,850,660 A | 12/1998 | O'Halloran | 15/195 |
| 5,867,856 A | 2/1999 | Herzog | 15/22.4 |
| D411,769 S | 7/1999 | Wright | D4/101 |
| 5,974,615 A | 11/1999 | Schwartz-Hartmann et al. | 15/22.4 |
| 6,000,083 A | 12/1999 | Blaustein et al. | 15/28 |
| 6,009,589 A | 1/2000 | Driesan et al. | 15/167.1 |
| 6,021,538 A | 2/2000 | Kressner et al. | 15/28 |
| 6,058,541 A | 5/2000 | Masterman et al. | 15/28 |
| D436,254 S | 1/2001 | Kling et al. | D4/101 |
| 6,230,354 B1 | 5/2001 | Sproat | 15/28 |
| 6,230,717 B1 | 5/2001 | Marx et al. | 132/308 |
| D446,941 S | 8/2001 | Kraemer | D4/111 |
| D452,775 S | 1/2002 | Wright | D4/101 |
| 2001/0023516 A1 | 9/2001 | Driesen et al. | 15/167.1 |

FOREIGN PATENT DOCUMENTS

FR  2561883  4/1985
JP  5-137615  6/1993

*Primary Examiner*—Mark Spisich
(74) *Attorney, Agent, or Firm*—Ohlandt, Greeley Ruggiero & Perie, LLP

(57) ABSTRACT

A bristle disk for an electric toothbrush is provided. The bristle disk has a bristle carrier and bristles arranged in tufts disposed in an outer row, a middle row and an inner row. The outer row tufts are adapted for cleaning the gingival space between the teeth and gums. The middle row tufts are adapted for cleaning the surface of the teeth. The inner row tuft is adapted for cleaning the interproximal space between the teeth.

44 Claims, 6 Drawing Sheets

TOOTHBRUSH BRISTLE DISK

RELATED APPLICATION

This application claims priority in U.S. Provisional Application Ser. No. 60/261,452, filed Jan. 12, 2001, the disclosure of which is incorporated herein by reference.

BACKGROUND OF THE INVENTION

1. Field of the Invention

The present invention relates to toothbrush bristle disks. More particularly, the present invention relates to a toothbrush bristle disk adapted for rotation by a rotary electric toothbrush. The bristle disk of the present invention includes a novel arrangement of bristles and tufts effective to clean the teeth and gums of a user when rotated by an electric toothbrush.

2. Description of the Prior Art

U.S. Pat. No. 3,848,336 to Copelan provides electric toothbrushes that rotate a bristle disk or brush about an axis parallel to the longitudinal axis of the bristles. U.S. Pat. No. 5,577,285 to Drossler assigned on its face to Braun Aktiengesellschaft provides electric toothbrushes that have been made to move the brush in an oscillatory motion.

However, there is a need for an improvement to the bristle disks used with such rotary electric toothbrushes. The present invention relates to such an improved bristle disk. Namely, the present invention provides a bristle disk adapted to simultaneously clean the gingival space between the teeth and gums, the surface of the teeth, and the interproximal space between the teeth by such electric toothbrushes.

SUMMARY OF THE INVENTION

It is an object of the present invention to provide a bristle disk.

It is another object of the present invention to provide a bristle disk having three rows of tufts.

It is a further object of the present invention to provide a bristle disk having an outer row, a middle row and an inner row of tufts.

It is a still further object of the present invention to provide a bristle disk having an outer row of tufts adapted for cleaning the gingival space between the teeth and gums, a middle row of tufts adapted for cleaning the surface of the teeth, and an inner row of tufts adapted for cleaning the interproximal space between the teeth.

These and other objects and advantages of the present invention are achieved by a bristle disk for an electric toothbrush having a bristle carrier and at least three groups of tufts extending from the bristle carrier with each of the tufts having one or more bristles. Some of the tufts being a first group of tufts disposed in an outer row. Others of the tufts being a second group of tufts disposed in a middle row. Still others of the tufts being a third group of tufts disposed in an inner row. The tufts of the outer row having a height and shape adapted for cleaning the gingival space between teeth and gums. The tufts of the middle row having a height and shape adapted for cleaning the surface of the teeth. The inner row having at least one tuft with a height and shape adapted for cleaning the interproximal space between the teeth.

Preferably, the first group of tufts are of the same height, the second group of tufts alternate between tufts with bristles of the same height and tufts with bristles of differing height wherein the tufts with bristles of differing height form an inward incline, and the third group of tufts are located about at a center point of the bristle carrier and have bristles with differing height that form a point.

DETAILED DESCRIPTION OF THE INVENTION

Figure 1:
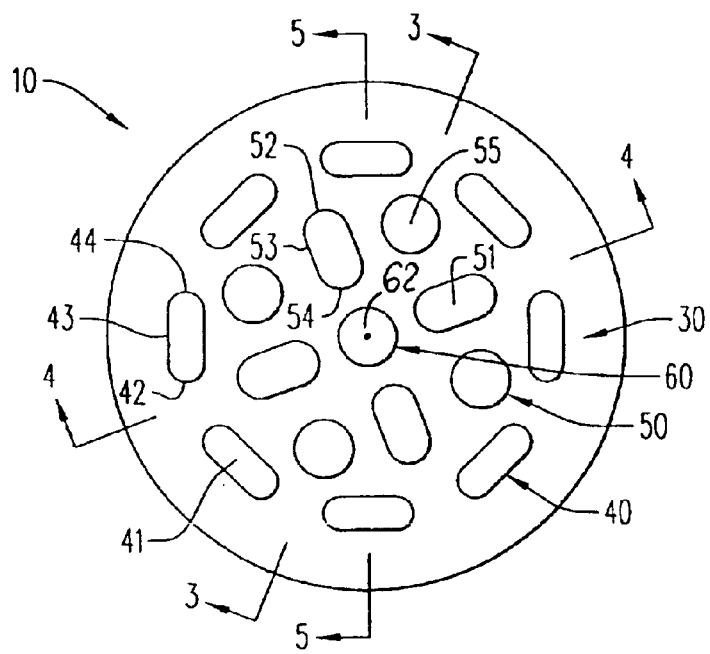
FIG. 1 is a top view of a bristle disk for rotary electric toothbrushes of the invention.

Referring to the figures and particularly to FIG. 1, a bristle disk generally represented by reference numeral 10 is shown. Disk 10 is a brush that is adapted to be disposed upon and rotatably engage a brush section (not shown). The brush section can have a first end adapted to engage a handle and a second, opposite end in which disk 10 is received (not shown). Disk 10, when used in conjunction with such a rotary toothbrush, is adapted to clean the teeth and gums of a user by being rotated about axis A shown in FIG. 2.

Figure 2:
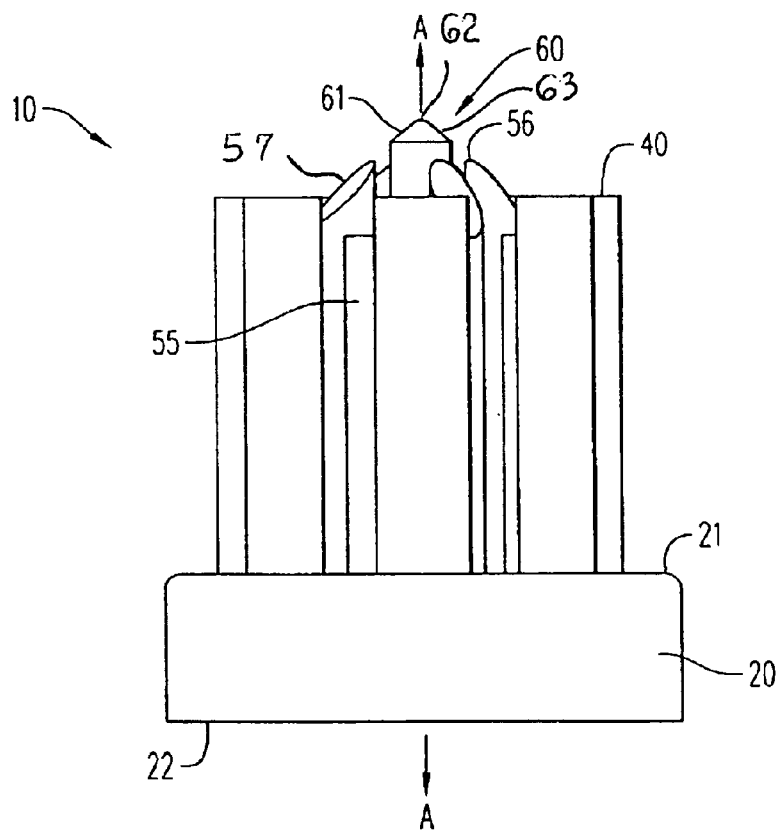
FIG. 2 is a side view of the bristle disk of FIG. 1.
Figure 3:
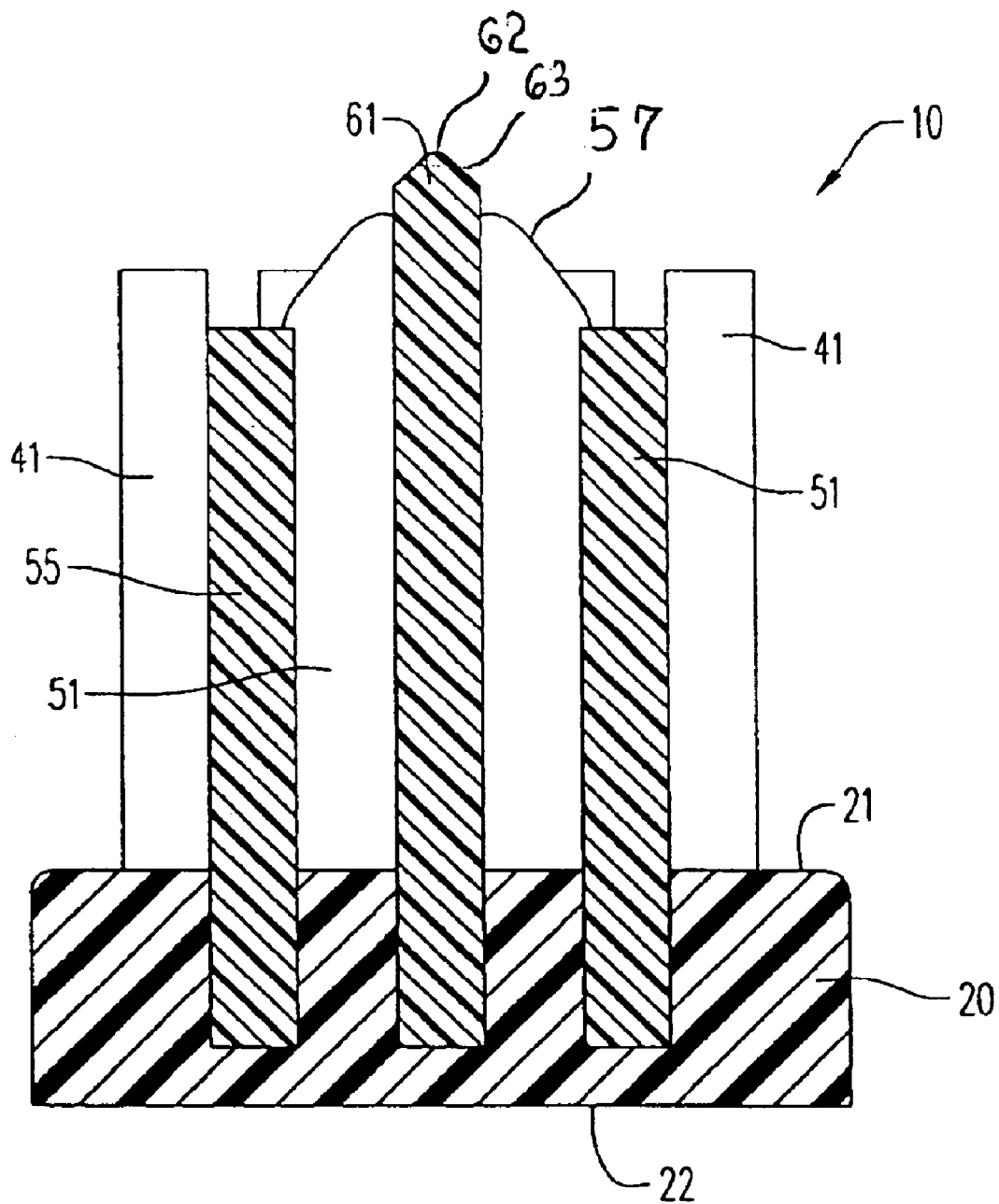
FIG. 3 is a sectional view of the bristle disk of FIG. 1 taken along line 3—3 of FIG. 1.
Figure 4:
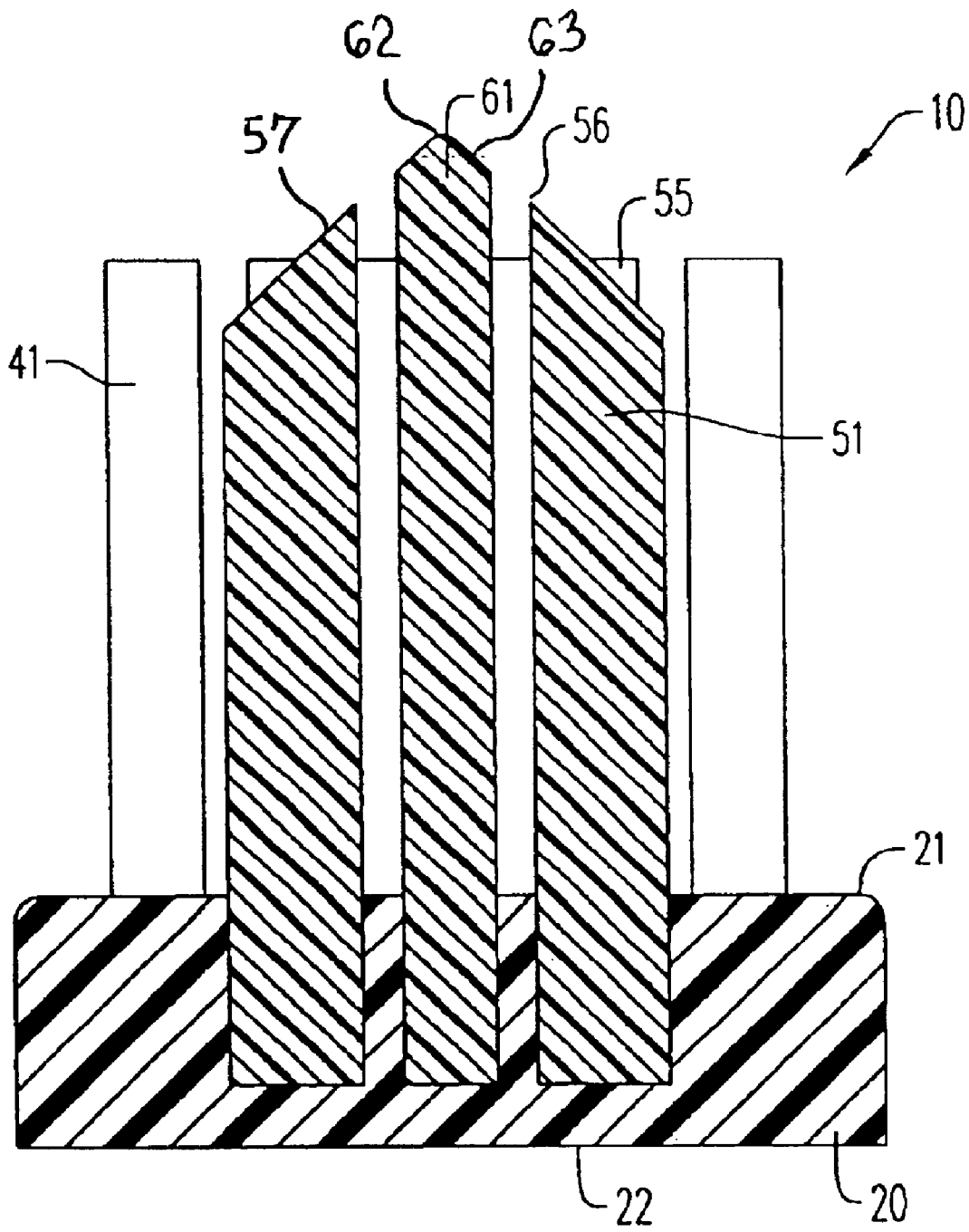
FIG. 4 is a sectional view of the bristle disk of FIG. 1 taken along line 4—4 of FIG. 1.
Figure 5:
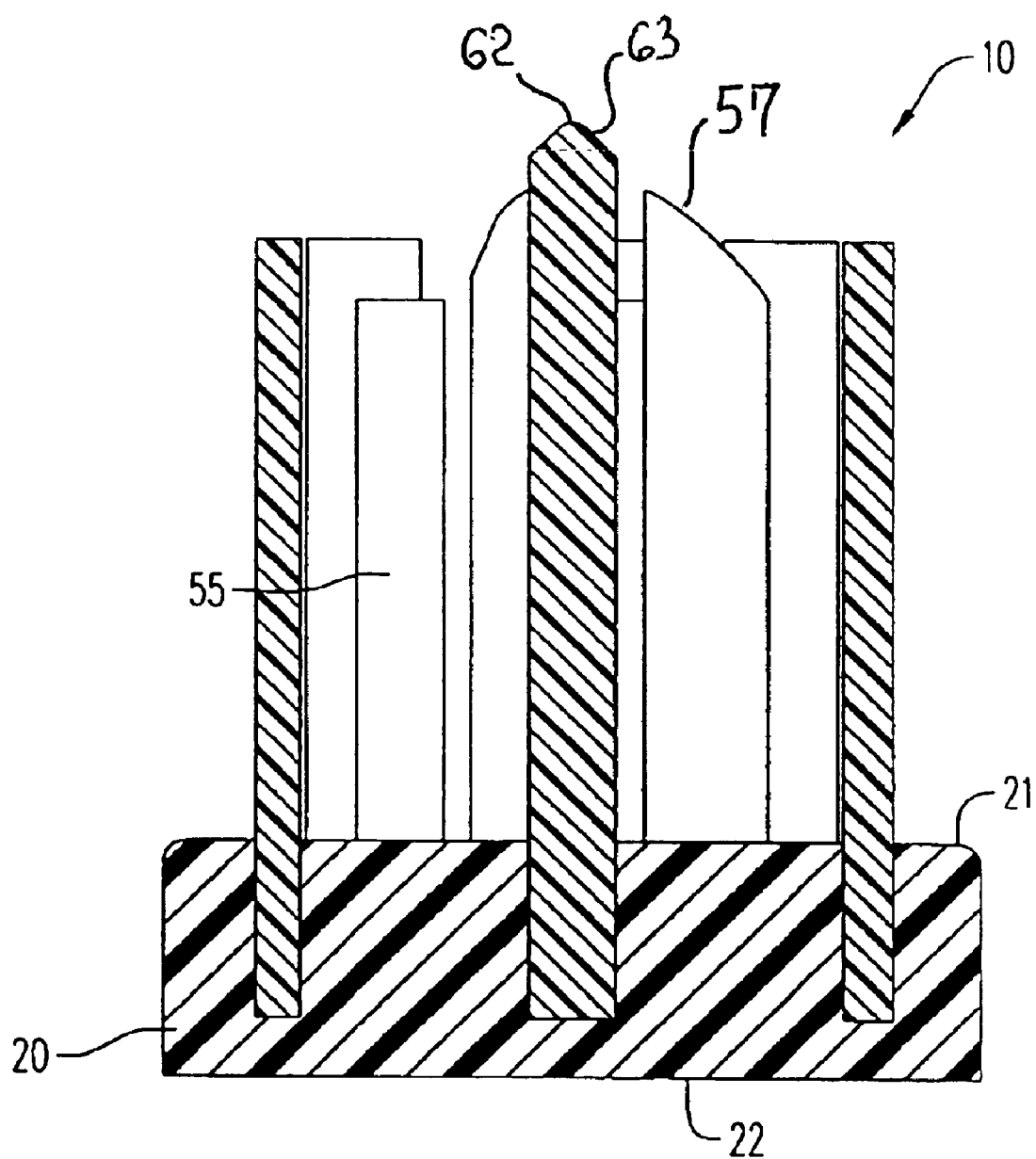
FIG. 5 is a sectional view of the bristle disk of FIG. 1 taken along line 5—5 of FIG. 1.
Figure 6:
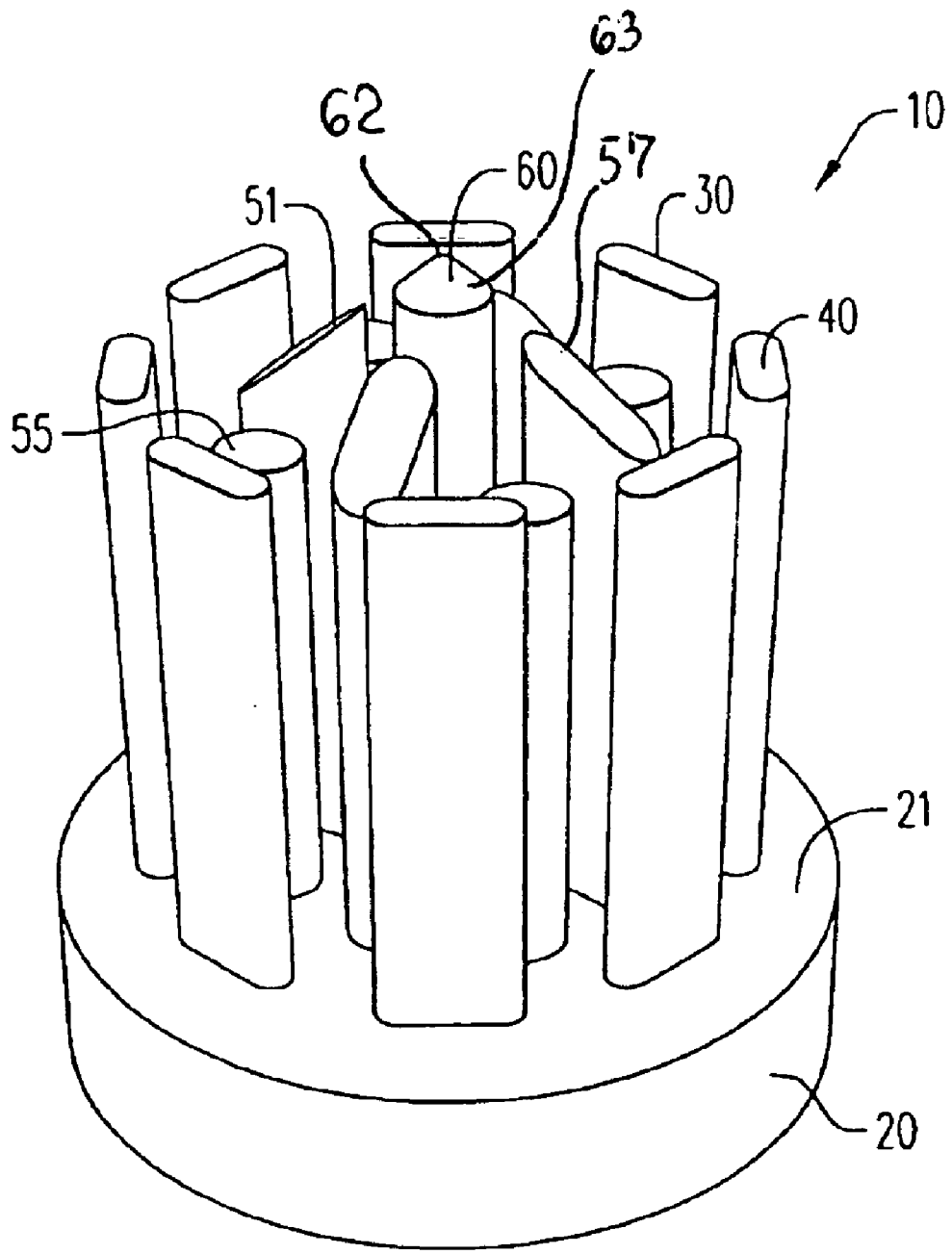
FIG. 6 is a perspective view of the bristle disk of FIG. 1.

Referring to FIGS. 1 and 2, disk 10 has an annular base 20 with a plurality of tufts 30 of bristles that extend from a bristle side 21 of the base. Base 20 also has a connecting side 22. Connecting side 22 has a connector (not shown), such as, but not limited to, a press fit coupler, for connecting disk 10 to the second end of the brush section of the toothbrush.

Each tuft 30 has one or more individual bristles. A tuft is a grouping of one or more bristles. A bristle is a single strand, piece or fiber of material. The bristles in each tuft 30 have substantially the same diameter or cross-section. However, it is possible that some bristles of a tuft 30 may have a different cross-section or diameter. While it is preferred that the diameter of each be circular, the bristle can have any geometric shape, such as, for example, a diamond, octagon, and pentagon. Also, the end of each bristle may have an embossment. The embossment may have a variety of patterns or shapes, such as, for example, protrusions or indentations.

In a preferred embodiment, each bristle of each tuft 30 of disk 10 is made of nylon, polyester, or other synthetic materials. Preferably, each bristle is made of nylon or polyester.

Tufts 30, and thus the bristles in each tuft, extend from base 20 in rows. Preferably, there are at least three groups of tufts 30. These groups of tuft 30 are an outer row 40, a middle row 50 and an inner row 60. More preferably, rows 40, 50, 60 are circumferential. Outer row 40 is intended to clean the gingival space between the teeth and gums. Middle row 50 is intended to clean the surface of the teeth. Inner row 60 is intended to clean the interproximal space between the teeth.

The bristles of each tuft 30 in outer row 40 are arranged such that each tuft is an elongated rectangular tufts 41 are arranged such that long side 43 is approximately perpendicular to the radius of outer row 40, and short side 44 is approximately parallel to the radius of the outer row. As shown in FIGS. 2 through 5, all of the bristles of rectangular tufts 41, and therefor all of the tufts in outer row 40, are of substantially the same height. Thus, outer row 40 is intended to clean the gingival space between the teeth and gums when base 20 is rotated by an electric toothbrush.

In a preferred embodiment, outer row 40 has eight rectangular tufts 41. However, any number of rectangular tufts 41 sufficient to clean the gingival space between the teeth and gums is considered within the scope of the present invention. In an alternate embodiment, long sided 43 of rectangular tufts 41 are curved so as to approximate the circumference of outer row 40.

Middle row 50 has two types of tufts. These types of tufts are rectangular tufts 51 and circular tufts 55. Middle row 50 includes an equal number of rectangular tufts 51 and circular tufts 55. Moreover, the tufts of middle row 50 alternate along the circumference of the middle row between rectangular tufts 51 and circular tufts 55. In a preferred embodiment, middle row 50 has eight tufts, namely four rectangular tufts 51 and four circular tufts 55. However, any number of alternating rectangular tufts 51 and circular tufts 55 sufficient to clean the surface of the teeth is considered within the scope of the present invention.

Rectangular tufts 51 of middle row 50 include rounded corners 52, a long side 53 and short side 54. Rectangular tufts 51 are arranged such that long side 53 is approximately parallel to the radius of middle row 50 and short side 54 is approximately perpendicular to the radius of the middle row. Additionally, rectangular tufts 51 have bristles of differing heights, which form a point 56. Point 56 of rectangular tufts 51 is formed along short side 54 closest to middle row 60. Thus as shown in FIGS. 2 through 5, rectangular tufts 51 have bristles that vary in height from short side 54 near outer row 40, to the short side near inner row 60 forming a linear slope 57 towards point 56.

Circular tufts 55 have bristles of substantially the same height to one another. Circular tufts 55 have rounded edges. The height of the bristles of circular tufts 55 is less than the height of any bristles in rectangular tufts 41. Thus, middle row 50 is intended to clean the surface of the teeth by providing an alternating circumferential row of rectangular tufts 51 and circular tufts 55 having alternating heights.

Inner row 60 preferably has a single center tuft 61. Tuft 61 is preferably circular. The bristles of center tuft 61 are arranged to form a point 62 in the center of brush disk 10. The height of the bristles at point 62 and edges 63 of center tuft 61 are larger than the height of any tuft in either the middle row 50 or outer row 40. Thus, inner row 60 is intended to clean the interproximal space between the teeth. In the present invention, each row may assist another row, besides functioning for its intended purpose.

As shown in FIG. 1, rectangular tufts 41 of outer row 40, are circumferentially offset from either rectangular tufts 51 or circular tufts 55 of middle row 50. Thus, tufts 30 are serially offset from a diameter of base 20.

Figure 7:
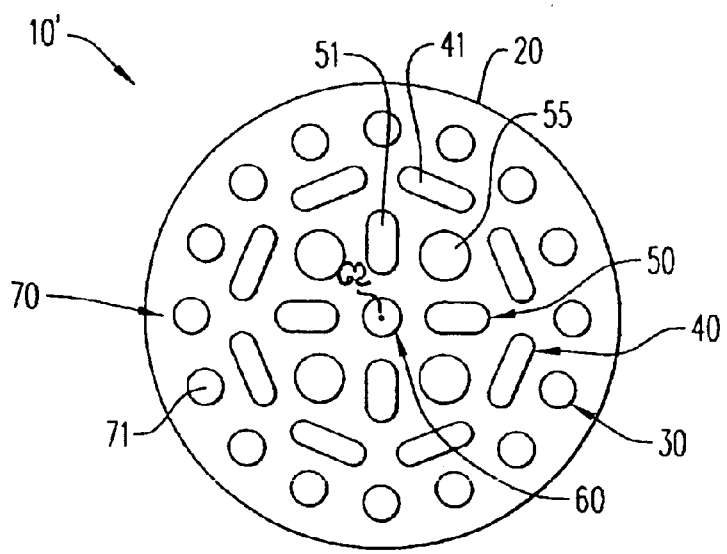
FIG. 7 is a top view of an alternative embodiment of the bristle disk of the present invention.

Referring to FIG. 7, an alternative embodiment of the bristle disk is generally represented by reference numeral 10'. Disk 10' has four groups of tufts 30. These groups of tufts 30 are peripheral row 70, an outer row 40, a middle row 50 and an inner row 60. Preferably, rows 40, 50, 60, 70 are circumferential. The bristles of each tuft 30 in peripheral row 70 are arranged such that each tuft is a substantially circular tuft 71.

Figure 8:
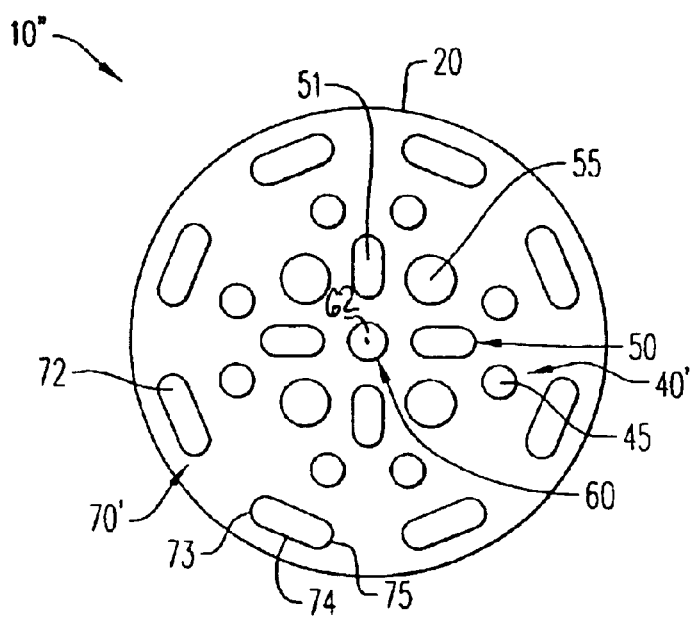
FIG. 8 is a top view of an alternative embodiment of the bristle disk of the present invention.

Referring to FIG. 8, an alternative embodiment of the bristle disk is generally represented by reference numeral 10". Disk 10" has four groups of tufts 30. These groups of tufts 30. are a peripheral row 70', an outer row 40', a middle row 50 and an inner row 60. Preferably, rows 40', 50, 60, 70' are circumferential. The bristles of each tuft 30 in peripheral row 70' are arranged such that each tuft is an elongated rectangular tuft 72. Each rectangular tuft 72 includes rounded corners 73, a long side 74 and a short side 75. The rectangular tufts 72 are arranged such that long side 74 is approximately perpendicular to the radius of peripheral row 70', and short side 75 is approximately parallel to the radius of the peripheral row. The bristles of each tuft 30 in outer row 40' are arranged such that each tuft is a substantially circular tuft 45.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A bristle disk for an electric toothbrush comprising:
   a bristle carrier; and
   a plurality of bristles arranged in at least three groups of tufts, said tufts extending from said bristle carrier, some of said tufts being a first group of tufts, said first group of tufts being disposed in an outer row on said bristle carrier, said first group of tufts being of the same height;
   others of said tufts being a second group of tufts, said second group of tufts forming a middle row on said bristle carrier, said second group of tufts alternating between tufts with bristles of the same height and tufts with bristles of differing height wherein said tufts with bristles of differing height form an inward incline; and
   still others of said tufts being a third group of tufts, said third group of tufts located about at a center point of said bristle carrier, said third group of tufts having bristles with differing height and forming a point.

2. The bristle disk of claim 1, wherein said plurality of bristles are substantially circular.

3. The bristle disk of claim 2, wherein said plurality of bristles have the same diameter.

4. The bristle disk of claim 1, wherein said plurality of bristles have a proximal end and a distal end, wherein said distal end has an embossment.

5. The bristle disk of claim 1, wherein said plurality of bristles are made of nylon or polyester.

6. The bristle disk of claim 1, wherein said first group of tufts are eight tufts.

7. The bristle disk of claim 1, wherein said second group of tufts are eight tufts.

8. The bristle disk of claim 1, wherein said first group of tufts are circumferentially offset from said second group of tufts.

9. The bristle disk of claim 1, wherein said third group of tufts is a single tuft that is circular.

10. The bristle disk of claims 1, wherein said point has a height greater than the height of said first group of tufts and said second group of tufts.

11. The bristle disk of claim 1, wherein said first group of tufts are rectangular and have long sides and short sides.

12. The bristle disk of claim 11, wherein said first group of tufts have rounded corners.

13. The bristle disk of claim 11, wherein said long sides are substantially perpendicular to a radius of said bristle carrier and said short sides are substantially parallel to said radius.

14. The bristle disk of claim 11, wherein said long sides are outwardly curved.

15. The bristle disk of claim 14, wherein said long sides have a radius of curvature that is about equal to a radius of said outer row.

16. The bristle disk of claim 1, wherein said second group of tufts with bristles of the same height form circular tufts.

17. The bristle disk of claim 16, wherein said second group of tufts that are circular tufts are shorter than said first group of tufts and said third group of tufts.

18. The bristle disk of claim 1, wherein said second group of tufts that have differing height form rectangular tufts with long sides and short sides.

19. The bristle disk of claim 18, wherein said rectangular tufts have rounded corners.

20. The bristle disk of claim 18, wherein said long sides are substantially parallel to a radius of said bristle carrier and said short sides are substantially perpendicular to said radius.

21. The bristle disk of claim 18, wherein said long sides are outwardly curved.

22. The bristle disk of claim 21, wherein said long sides have a radius of curvature that is about equal to a radius of curvature of said middle row.

23. A brush section for an electric toothbrush having a handle section, the brush section comprising:
 a body having a first end adapted to be connected to the handle section and a second end remote from said first end, and
 a bristle disk rotatably engageable with said second end, wherein said bristle disk comprises:
  a bristle carrier; and
  a plurality of bristles arranged in at least three groups of tufts, said tufts extending from said bristle carrier, some of said tufts being a first group of tufts, said first group of tufts being disposed in an outer row on said bristle carrier, said first group of tufts being of the same height;
  others of said tufts being a second group of tufts, said second group of tufts forming a middle row on said bristle carrier, said second group of tufts alternating between tufts with bristles of the same height and tufts with bristles of differing height wherein said tufts with bristles of differing height form an inward incline; and
  still others of said tufts being a third group of tufts, said third group of tufts located about at a center point of said bristle carrier, said third group of tufts having bristles with differing height and forming a point.

24. The brush section of claim 23, wherein said plurality of bristles are substantially circular.

25. The brush section of claim 24, wherein said plurality of bristles have the same diameter.

26. The brush section of claim 23, wherein said plurality of bristles have a proximal end and a distal end, wherein said distal end has an embossment.

27. The brush section of claim 23, wherein said plurality of bristles are made of nylon or polyester.

28. The brush section of claim 23, wherein said first group of tufts are eight tufts.

29. The brush section of claims 23, wherein said second group of tufts are eight tufts.

30. The brush section of claim 23, wherein said first group of tufts are circumferentially offset from said second group of tufts.

31. The brush section of claim 23, wherein said third group of tufts is a single tuft that is circular.

32. The brush section of claim 23, wherein said point has a height greater than the height of said first group of tufts and said second group of tufts.

33. The brush section of claim 23, wherein said first group of tufts are rectangular and have long sides and short sides.

34. The brush section of claim 33, wherein said first group of tufts have rounded corners.

35. A The brush section of claim 33, wherein said long sides are substantially perpendicular to a radius of said bristle carrier and said short sides are substantially parallel to said radius.

36. The brush section of claim 33, wherein said long sides are outwardly curved.

37. The brush section of claim 36, wherein said long sides have a radius of curvature that is about equal to a radius of said outer row.

38. The brush section of claim 23, wherein said second group of tufts with bristles of the same height form circular tufts.

39. The brush section of claim 38, wherein said second group of tufts that are circular tufts are shorter than said first group of tufts and said third group of tufts.

40. The brush section of claim 23, wherein said second group of tufts that have bristles of differing height form rectangular tufts with long sides and short sides.

41. The brush section of claim 40, wherein said rectangular tufts have rounded corners.

42. The brush section of claim 40, wherein said long sides are substantially parallel to a radius of said bristle carrier and said short sides are substantially perpendicular to said radius.

43. The brush section of claim 40, wherein said long sides are outwardly curved.

44. The brush section of claim 43, wherein said long sides have a radius of curvature that is about equal to a radius of curvature of said middle row.

* * * * *